United States Patent [19]
Beckstead et al.

[11] Patent Number: 6,028,719
[45] Date of Patent: Feb. 22, 2000

[54] 360 DEGREE/FORWARD VIEW INTEGRAL IMAGING SYSTEM

[75] Inventors: Jeffrey A. Beckstead, Sand Lake; Steven R. Nordhauser, Troy, both of N.Y.

[73] Assignee: InterScience, Inc., Troy, N.Y.

[21] Appl. No.: 09/165,082

[22] Filed: Oct. 2, 1998

[51] Int. Cl.[7] .......................... G02B 13/06; G02B 17/00; G02B 27/10
[52] U.S. Cl. .......................... 359/725; 359/618; 359/726
[58] Field of Search .................... 359/618, 725, 359/626, 627, 726

[56] References Cited

U.S. PATENT DOCUMENTS

| | | | |
|---|---|---|---|
| 3,846,809 | 11/1974 | Pinzone et al. | 354/95 |
| 4,072,427 | 2/1978 | Alsberg | 356/241 |
| 4,395,093 | 7/1983 | Rosendahl et al. | 350/441 |
| 4,423,422 | 12/1983 | Knop et al. | 343/786 |
| 4,429,957 | 2/1984 | King | 350/423 |
| 4,492,438 | 1/1985 | Clegg | 350/432 |
| 4,607,925 | 8/1986 | Kamigaichi et al. | 354/63 |
| 4,779,955 | 10/1988 | Schmanski | 350/97 |
| 4,849,622 | 7/1989 | Beggs | 250/216 |
| 4,855,820 | 8/1989 | Barbour | 358/100 |
| 4,899,277 | 2/1990 | Iizuka et al. | 364/422 |
| 5,016,995 | 5/1991 | Pullen, V | 350/537 |
| 5,195,392 | 3/1993 | Moore et al. | 73/866.5 |
| 5,238,210 | 8/1993 | Heitzmann | 244/158 R |
| 5,381,784 | 1/1995 | Adair | 128/6 |
| 5,473,474 | 12/1995 | Powell | 359/725 |
| 5,512,034 | 4/1996 | Finn et al. | 600/138 |
| 5,631,778 | 5/1997 | Powell | 359/724 |
| 5,652,617 | 7/1997 | Barbour | 348/85 |
| 5,760,826 | 6/1998 | Nayar | 348/36 |
| 5,781,649 | 7/1998 | Brezoczky | 382/108 |
| 5,905,595 | 5/1999 | Minami | 359/618 |

OTHER PUBLICATIONS

S.B. Fair and J.A. Gilbert, "Panoramic Endoscopy", SPIE Proceedings, vol. 1649, Jan. 1992, 203–207.

S. Zimmerman and D. Kuban, "A Video Pan/Tilt/Magnify/Rotate System with no Moving Parts", Proceedings of IEEE/AIAA 11th Digital Avionics Systems Conference, 1992, 523–531.

E.L. Hall and Z.L. Cao, "Omnidirectional Viewing Using a Fisheye Lens", SPIE Procceedings, vol. 728, 1986, 250–256.

P. Greguss, "Panoramic Security", SPIE Proceedings, vol. 1509, Oct. 1991, 55–66.

D.R. Matthys, J.A. Gilbert, and J. Puliparambil, "Endoscopic Inspection Using a Panoramic Annular Lens", SPIE Proceedings, vol. 1554B, Dec. 1991, 736–742.

*Primary Examiner*—Hung Xuan Dang
*Assistant Examiner*—Suzanne Letendre
*Attorney, Agent, or Firm*—Jay R. Yablon

[57] ABSTRACT

A 360 Degree Forward View Integral Imaging System comprises a panoramic imaging element capable of imaging a full 360 degree panoramic image and a forward image onto a single plane. This system can be integrated with a variety of image capture systems such as a CCD camera, a film based camera, or a fiber optic bundle coupled to a CCD camera for remote imaging. The applications of such a system include but are not limited to pipe inspection, bore hole inspection and remote imaging.

30 Claims, 6 Drawing Sheets

360 DEGREE/FORWARD VIEW INTEGRAL IMAGING SYSTEM

"This invention was made with U.S. Government support under contract #F29601-97-C-0105 awarded by the Department of the United States Air Force. The government has certain rights in the invention."

FIELD OF THE INVENTION

This invention relates to the field of panoramic imaging systems, and particularly to panoramic imaging systems capable of capturing a full 360 degree view as well as a forward view in a single image without mechanical movement of the optical elements.

BACKGROUND OF THE INVENTION

Panoramic imaging systems are common in a variety of applications including medical endoscopy, surveillance, bore hole inspection, and pipe inspection. Panoramic imaging allows for a full radial view of the surroundings usually from a single point. In the example of pipe inspection, the integrity of the interior pipe wall can be inspected by feeding an imaging system down the center of the pipe to view the interior wall. Panoramic imaging can be achieved in a variety of ways as established by the details of the prior art described below.

U.S. Pat. Nos. 5,652,617 and 4,855,820 disclose bore hole video inspection systems that comprising two completely independent imaging systems, one for forward viewing and the other for side viewing. The forward-viewing imaging system comprises a forward-facing video camera with a wide angle lens. The side viewing imaging system comprises a forward facing video camera with a gyroscopically controlled angular mirror and lens system for viewing 50 degree segments of the side view with the camera. The gyroscope rotates to collect the entire 360 degree radial image.

The primary applications for panoramic imaging systems such as these is the inspection of pipelines, tubing or bore holes. There are many important aspects of obtaining reliable and useful imaging data. Ease of tracking and identifying imaging locations is a critical factor in using the acquired images to repair damaged areas. Imaging systems that sweep the view and acquire multiple images throughout the entire 360 degree sweep have several disadvantages. For example, in tight remote spaces, moving parts are difficult to control and are also subjected to repeated wear leading to eventual failure. Multiple images require reconstruction in image post-processing to create the full 360 degree view. Overlap of image fields wastes storage capacity, but without it risks are taken in missing critical views and important information. And location tracking in these systems is often difficult.

OBJECTS OF THE INVENTION

Therefore, it is the object of the invention disclosed herein to provide a new and improved imaging system for simultaneous forward and 360 degree panoramic viewing.

It is a further object of the invention to provide an imaging system for simultaneous forward and 360 degree panoramic viewing that does not require mechanical motion.

It is a further object of the invention to facilitate identification of imaging locations.

It is a further object of the invention to acquire the 360 degree panoramic view and the forward view without any moving parts.

It is a further object of the invention to present the 360 degree panoramic view to an associated imaging system as a non-segmented image field.

It is a further object of the invention to provide imaging from the forward view in combination with the panoramic view, in a single, non-segmented image field.

SUMMARY OF THE INVENTION

The present invention provides a compound imaging system for 360 degree and forward imaging that improves the prior art as noted above. The present invention comprises a panoramic imaging element capable of imaging a full 360 degree panoramic image and a forward image onto a single imaging plane. This panoramic imaging element is configured to project a "donut"-shaped image into the imaging plane wherein the "hole" of the donut contains the forward image and the "body" of the donut contains the panoramic image.

While this system is described and illustrated as integrated to a CCD camera, this does not in any way limit the disclosure limited to use in combination with a CCD camera. Indeed, this system is applicable to any image recording device that accepts its initial input imaging information from an image optically projected along a single plane. Thus, for example, this system can be integrated with a variety of image capture systems such as a CCD camera, a vidicon, a film based camera, or—for remote imaging—a fiber optic bundle coupled to a CCD or other camera. All such combinations are encompassed by this disclosure and its associated claims.

The present invention acquires the 360 degree panoramic image without moving parts and presents it in a non-segmented image field for capture. Additionally, the present invention provides imaging from the forward view, also non-segmented from (in the same imaging plane as) the panoramic image. The forward view is critical in pipe inspection or similar applications for purposes of location identification or just additional data collection. The applications of this system include but are not limited to pipe inspection, bore hole inspection, surveillance, and remote imaging.

BRIEF DESCRIPTION OF THE DRAWINGS

The features of the invention believed to be novel are set forth in the associated claims. The invention, however, together with further objects and advantages thereof, may best be understood by reference to the following description taken in conjunction with the accompanying drawings in which:

DETAILED DESCRIPTION

Figure 1:
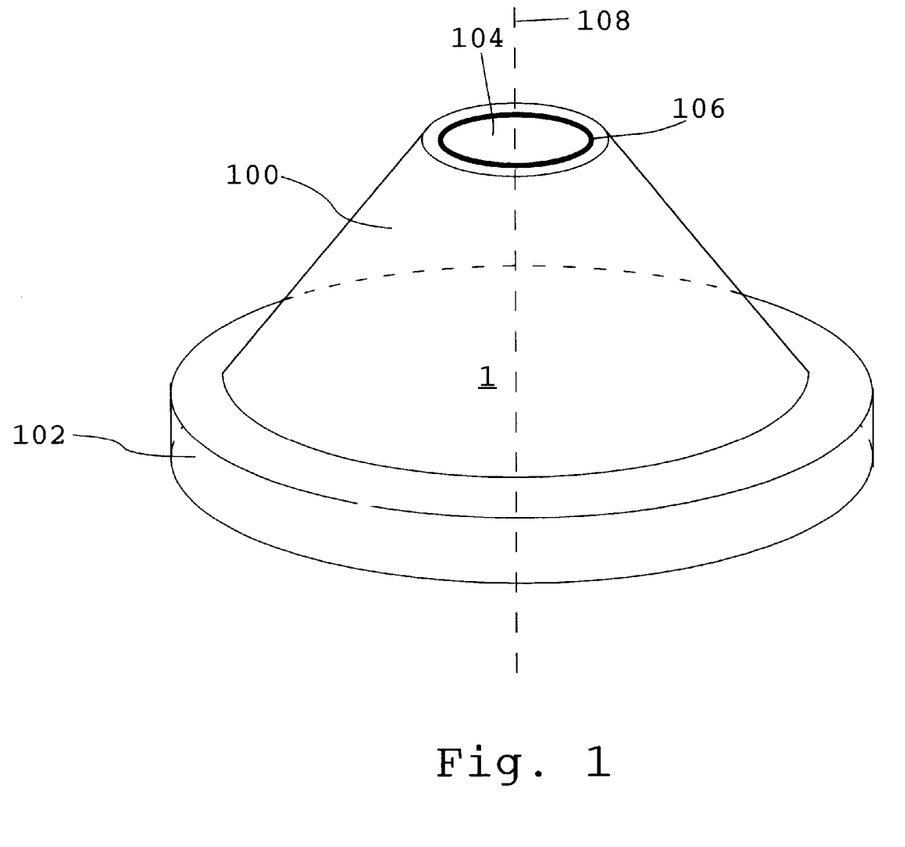
FIG. 1 is a forward perspective view of the panoramic imaging element.
Figure 2:
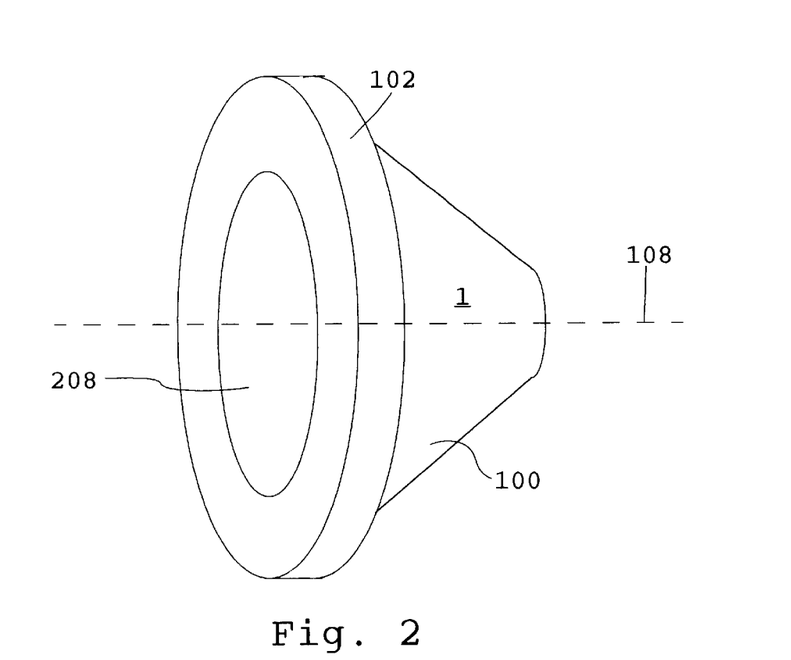
FIG. 2 is a rearward perspective view of the panoramic imaging element.

The present invention comprises a panoramic imaging element 1 capable of imaging a 360 degree panoramic image and a forward image onto a single plane. FIGS. 1 and 2 are forward and rearward perspective views of panoramic imaging element 1 showing all of its primary features.

As seen in FIG. 1, panoramic imaging element 1 comprises a conic mirror reflective upon its outer surface, and fully symmetric about central axis of symmetry 108. If a cross section is taken from FIG. 1 along a cross-sectional plane that includes all of central symmetry axis 108 (such as is later illustrated in FIG. 3), the intersection of this cross-sectional plane with the outer surface of conic mirror 100 will define a line. This will be referred to by saying that a symmetric planar cross section of conic mirror 100 defines a line, or more concisely, that conic mirror 100 comprises a linear symmetric cross section. However, while FIG. 1 illustrates a linear symmetric cross section for conic mirror 100, it is to be understood that the symmetric cross section of conic mirror 100 can be of various geometries such as but not limited to linear, parabolic, hyperbolic, spherical, elliptical, or any combination thereof. The particular geometry chosen for this symmetric cross section will depend on the optical considerations of the given application.

The center of conic mirror 100 is bored out from top to bottom along central axis 108 for the placement of additional optical components. The base of the conic mirror 100 is secured to base holder 102. Focusing element 104 is secured in the bored out center at the top (apex) of conic mirror 100 by focusing element support 106. Opposite the apex of the cone along the central symmetry axis is a wide region of the cone, as illustrated.

Similarly, FIG. 2 shows perspective view of panoramic imaging element 1, but from the rear. Base holder 102 supports conic mirror 100 and a transparent optical element 208. The interior of imaging element 1 defines a hollow cavity 300 as denoted in FIG. 3. Transparent optical element 208 seals the optical elements within hollow cavity 300 to prevent excessive exposure to dust and unnecessary particulates, and is transparent so that light can pass unobstructed through transparent optical element 208 to impinge upon and be focused by focusing element 104 shown in FIG. 1. Typically, transparent optical element 208 is a transparent window that has substantially no effect on the passing light. However, in some alternative embodiments where the position of focusing element 104 is altered, transparent optical element 208 can alternatively be a lens to aid focusing element 104 in the image transmission.

Figure 3:
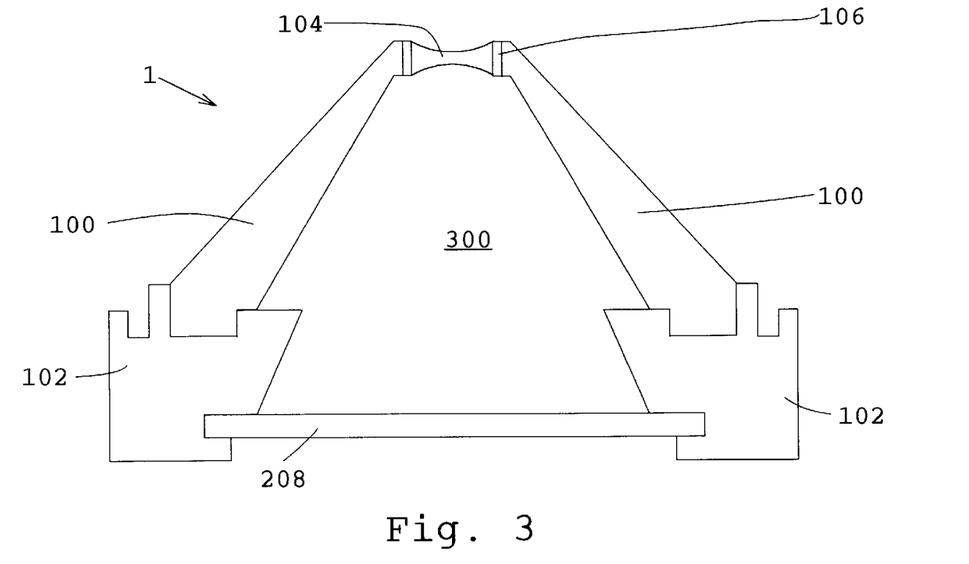
FIG. 3 is a cross-sectional view of the panoramic imaging element.

For additional reference and clarity, panoramic imaging element 1 is shown in cross-section in FIG. 3. The relative positioning of focusing element 104 with respect to conic mirror 100 and transparent optical element 208 is evident. In addition, the interfaces between conic mirror 100 and transparent optical element 208 via base holder 102, and between conic mirror 100 and focusing element 104 via focusing element support 106, are evident.

Figure 4:
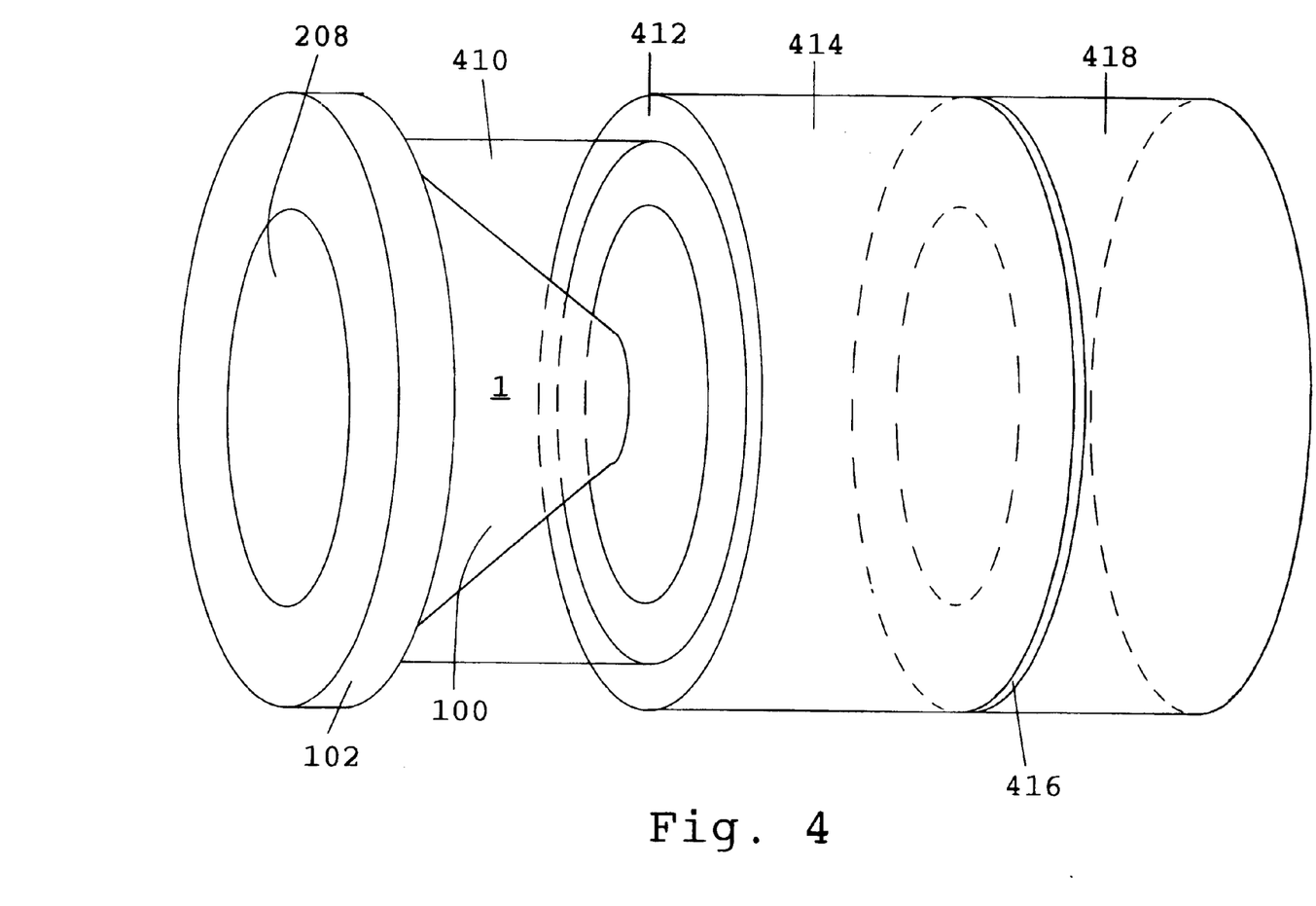
FIG. 4 is a perspective view of the 360 degree forward view imaging system adapted to a CCD camera.

FIG. 4 is a perspective view of panoramic imaging element 1 utilized in a 360 degree/forward viewing application integrated to a CCD camera. As described in FIG. 1, conic mirror 100 is secured to base holder 102 which also supports transparent optical element 208. Here, a transparent cylinder 410 is also secured to base holder 102 so as to surround the entire circumference of conic mirror 100 in order to provide imaging access to the entire 360 degree perimeter. Thus, light from outside the entire 360 degree circumference of transparent cylinder 410 is enabled to pass through transparent cylinder 410, and impinge upon and be reflected by the reflective outer surface of conic mirror 100. Proximate the front region (near focusing element 104) of conic mirror 100, the transparent cylinder 410 is secured to support structure 412 which in turn is secured to coupling cylinder 414. The coupling cylinder 414 is secured on its opposite end to coupling plate 416, which is in turn secured to image detection means 418 which in this illustration is a CCD camera housing.

Figure 5:
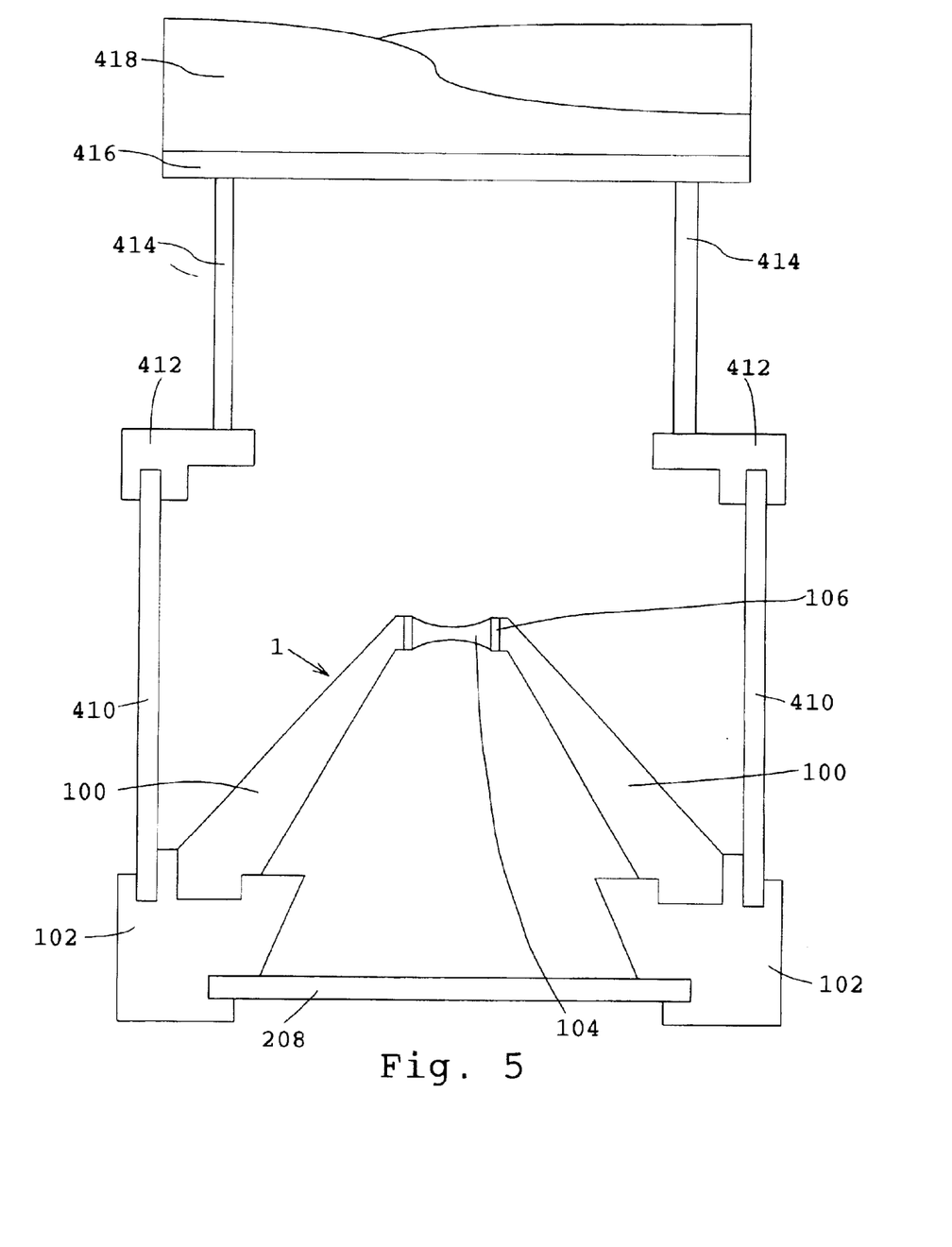
FIG. 5 is a cross-sectional view of the panoramic imaging element in conjunction with an imaging system.

The specific layout of the components detailed in FIG. 4 can best be described with reference to the cross-sectional view of FIG. 5 which shows the panoramic imaging element in conjunction with an imaging system. Referring to FIG. 5, conic mirror 100 is secured to base holder 102, which also provides support to transparent optical element 208 and transparent cylinder 410. At the apex (front) of conic mirror 100, focusing element 104 is secured in the central bore hole by focusing element support 106. At the end opposite base holder 102, transparent cylinder 410 is secured to support structure 412 which provides a means of connectivity to the chosen detection system. Coupling cylinder 414 connects support structure 412 to coupling plate 416 which in turn provides the interface to image detection means 418 which in this illustration, again, is CCD camera housing.

Figure 6:
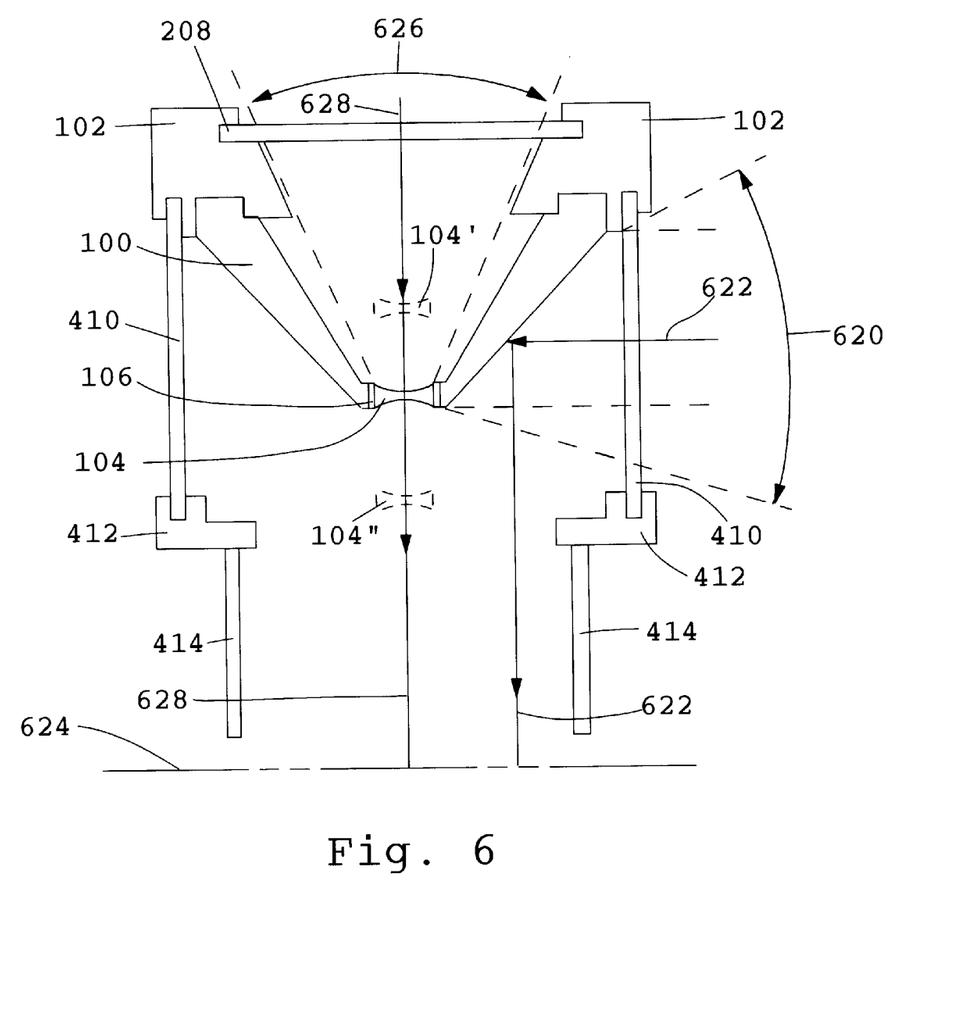
FIG. 6 is a cross-sectional view of the 360 degree forward view imaging system as adapted to a CCD camera.

The optical operation of the present invention is best described with reference to FIG. 6 in which it is utilized to provide an image to the CCD camera of a full 360 degree panoramic view as well as a forward view. FIG. 6 illustrates the approximate optical paths in the imaging system.

Conic mirror 100 collects image information from panoramic field of view 620. Although FIG. 6 represents the optical paths in cross-section only, panoramic field of view 620 circumnavigates the entire perimeter of conic mirror 100. Panoramic optical path 622 shows a representative light path from within the panoramic field of view 620, as it passes through transparent cylinder 410, and reflects off of conic mirror 100 onto imaging plane 624.

Similarly, focusing element 104 collects image information from forward field of view 626. Forward optical path 628 shows a representative light path from within forward field of view 626, as it passes through transparent optical element 208 and focusing element 104, to be focused upon imaging plane 624.

This system is thus designed such that all optical information from both the panoramic field of view 620 and the forward field of view 626 is delivered to a single imaging plane 624, for capture by a single image detection means 418. The preferred embodiment of this invention utilizes a CCD camera as image detection means 418. However, alternative embodiments can utilize other means of detection such as but not limited to vidicons, film based cameras, fiber optic bundles, or direct viewing imaging systems. The use of a single detection means, however, requires strict optical system design. The desired application would influence the desired depths of the panoramic field of view 620 and forward field of view 626 and thus have direct influence over the diameter of transparent optical element 208, the length of transparent cylinder 410, the length of the coupling cylinder 414, the power and optical qualities of focusing element 104, and (to the degree needed to eliminate interference with forward field of view 626) the geometry of the hollow center 300 of conic mirror 100.

An alternative embodiment of the present invention places the focusing element 104 anywhere along central axis 108 of conic mirror 100 where it does not interfere with the panoramic field of view 620. Thus it can be placed deeper into hollow center 300 of the conic mirror 100 as illustrated by focusing element 104', or in front of conic mirror 100 with a support mechanism of its own as a location illustrated by focusing element 104". Although this introduces greater complexity into the mechanical design of the system, it might be necessary due to the optical requirements of a specific application.

Figure 7:
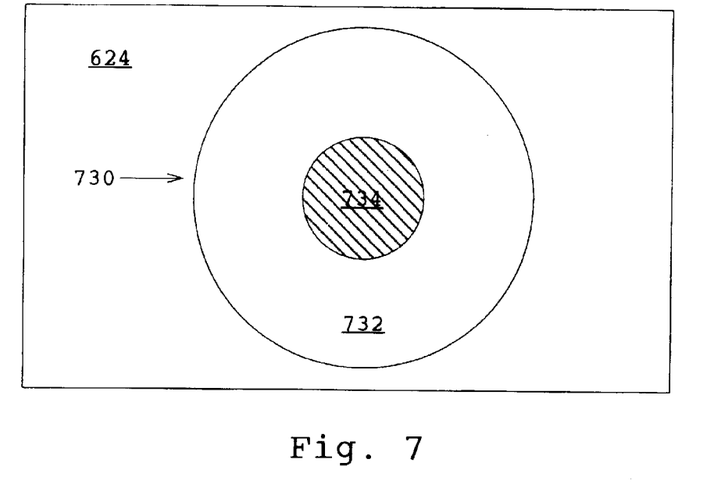
FIG. 7 is a view of the resultant image from the 360 degree/forward viewing system imaged with a rectangular imager.

As shown in FIG. 7, the preferred embodiment of the present invention produces a front and panoramic composite image 730 that lands upon imaging plane 624 for detection by the specified image detection means 418. Composite image 730 comprises a "donut"-shaped image 732 which originates from panoramic field of view 620, and round-shaped image 734 in the center "hole" of the donut, which originates from forward field of view 626. This type of image production lends itself to various image processing methods which convert the donut shaped image to a more usable image format.

Based on the specific geometry of conic mirror 100 (as per the earlier discussion of possible symmetric cross sections for the outer surface of conic mirror 100), the donut-shaped image information 732 presented at imaging plane 624 and detected by image detection means 418 will vary, and subsequently, will require various means of image processing. Specifically, image processing methods are used to correct and convert image distortions induced by the particular geometry of conic mirror 100 into at least one user-viewable image of substantially ordinary image proportions.

Figure 8A:
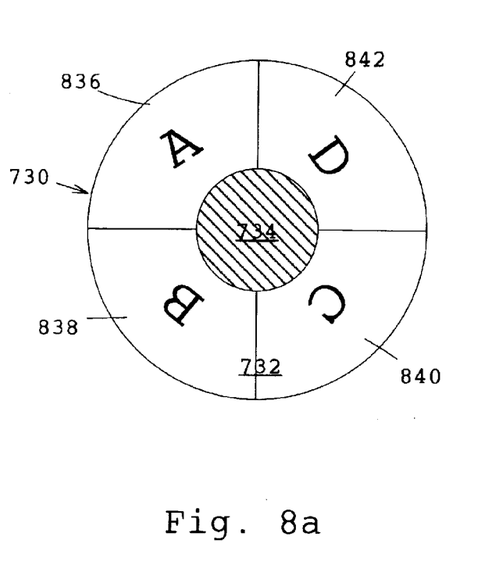
FIG. 8a is a pre-image processing view of the resultant image from the 360 degree/forward viewing system.
Figure 8B:
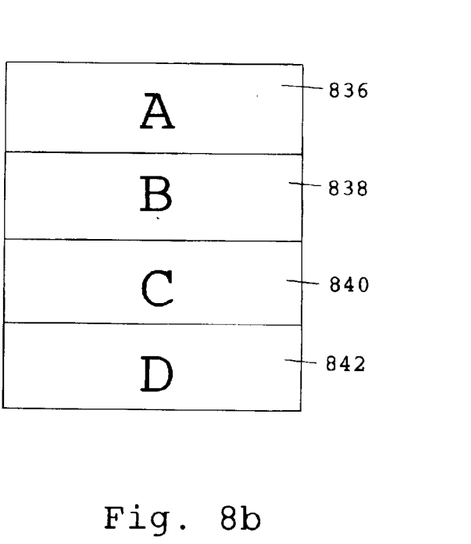
FIG. 8b is a post-image processing view of the resultant image from the 360 degree/forward viewing system.

Illustrated here as a means of example, FIGS. 8a and 8b depict a possible before and after image with the use of a suitable image processing method (that is, a suitable algorithm implemented by a suitable computer and/or electronic device means) to convert the donut shaped image 730 to a more user-friendly image. FIG. 8a shows image 730 comprising round image 734 and donut-shaped image 732 broken into 4 sectors; namely image sector A 836, image sector B 838, image sector C 840, and image sector D 842. Obviously the number of sectors that an image is divided into is purely arbitrary and can easily be manipulated in the image processing method. Four sectors are shown here merely as an illustrative example and therefore poses no limitations on the scope of this invention.

FIG. 8b illustrates the results of converting donut shaped image 732 of FIG. 8a into a more user-friendly format (i.e., into a user-viewable image of ordinary image proportion) using an image processing method designed to accommodate image 730 produced by the present invention. Image sectors 836, 838, 840, and 842, are rearranged to present more user friendly information, and together with round image 734 provide full panoramic and forward viewing information in a single presentation. The actual presentation of image sectors 836, 838, 840, and 842, is arbitrary as well. FIG. 8b shows them stacked as this is the presentation that would most easily be presented on a standard computer or display monitor. Alternatively the image sectors 836, 838, 840, and 842 can be presented side by side connecting adjacent image areas. Typically, no image manipulation would need to be done on round image 734 since it is a straight on view.

While only certain preferred features of the invention have been illustrated and described, many modifications, changes and substitutions will occur to those skilled in the art. It is, therefore, to be understood that this disclosure and its associated claims are intended to cover all such modifications and changes as fall within the true spirit of the invention.

We claim:

1. A panoramic imaging element comprising:

a conic mirror reflective on an outer surface thereof, and substantially symmetric about a central axis of symmetry passing therethrough, comprising an apex and a wide region thereof along said central axis of symmetry; and a focusing element secured proximate a bored-out center at said apex of said conic mirror, also substantially symmetric about said central axis of symmetry; wherein light from a panoramic view field is reflected off of the reflective outer surface of said conic mirror and onto an imaging plane substantially perpendicular to said central axis of symmetry, thereby forming a substantially donut-shaped image with a substantially round center hole on said imaging plane; and light from a forward view field passes through the wide region and an interior of said conic mirror, through said focusing element, and onto said imaging plane, thereby forming a substantially round-shaped image on said imaging plane, substantially within said center hole of said donut-shaped image.

2. The panoramic imaging element of claim 1, wherein a symmetric cross section of said reflective outer surface of said conic mirror is selected from the geometric group consisting of linear, parabolic, hyperbolic, spherical, and elliptical.

3. The panoramic imaging element of claim 1, wherein said focusing element is placed along said central axis of symmetry within said interior of said conic mirror.

4. The panoramic imaging element of claim 1, wherein said focusing element is placed along said central axis of symmetry outside of said interior of said conic mirror.

5. The panoramic imaging element of claim 1, wherein said focusing element is placed along said central axis of symmetry substantially within said bored out center at said apex of said reflective surface.

6. The panoramic imaging element of claim 1, as used in combination with a panoramic imaging system, further comprising:

image detection means detecting said substantially donut-shaped image and said substantially round-shaped image substantially within said center hole of said donut-shaped image on said imaging plane.

7. The panoramic imaging system of claim 6, wherein said image detection means comprises a CCD camera.

8. The panoramic imaging system of claim 6, wherein said image detection means comprises a film camera.

9. The panoramic imaging system of claim 6, wherein said image detection means comprises a fiber optic bundle coupled with a camera.

10. The panoramic imaging system of claim 6, wherein said image detection means comprises a vidicon.

11. The panoramic imaging system of claim 6, further comprising:

image processing means processing and converting said donut-shaped image detected by said image detection means into at least one user-viewable image of substantially ordinary image proportions.

12. The panoramic imaging system of claim 11, wherein said system is used to inspect pipes.

13. The panoramic imaging system of claim 11, wherein said system is used to inspect bore holes.

14. The panoramic imaging system of claim 11, wherein said system is used for surveillance.

15. The panoramic imaging system of claim 11, wherein said system is used for medical endoscopy.

16. A method of forming an imaging plane substantially perpendicular to a central axis of symmetry passing through a conic mirror substantially symmetric about said central axis of symmetry, said image plane comprising both panoramic view field and forward view field images, comprising the steps of:

forming said panoramic view field image by reflecting light from said panoramic view field off of a reflective outer surface of said conic mirror and onto said imaging plane, thereby forming a substantially donut-shaped image with a substantially round center hole on said imaging plane; and forming said forward view field image by passing light from said forward view field through a wide region and an interior of said conic mirror, through a focusing element proximate a bored-out center at an apex of said conic mirror, said focusing element also substantially symmetric about said central axis of symmetry, and onto said imaging plane, thereby forming a substantially round-shaped image on said imaging plane, substantially within said center hole of said donut-shaped image.

17. The method of claim 16, comprising the further step of selecting a symmetric cross section of said reflective outer surface of said conic mirror from the geometric group consisting of linear, parabolic, hyperbolic, spherical, and elliptical.

18. The method of claim 16, comprising the further step of placing said focusing element along said central axis of symmetry within said interior of said conic mirror.

19. The method of claim 16, comprising the further step of placing said focusing element along said central axis of symmetry outside of said interior of said conic mirror.

20. The method of claim 16, comprising the further step of placing said focusing element along said central axis of symmetry substantially within said bored out center at said apex of said reflective surface.

21. The method of claim 16, as used in combination with a panoramic imaging system, further comprising the step of:

detecting said substantially donut-shaped image and said substantially round-shaped image substantially within said center hole of said donut-shaped image on said imaging plane, using image detection means.

22. The method of claim 21, wherein said image detection means comprises a CCD camera.

23. The method of claim 21, wherein said image detection means comprises a film camera.

24. The method of claim 21, wherein said image detection means comprises a fiber optic bundle coupled with a camera.

25. The method of claim 21, wherein said image detection means comprises a vidicon.

26. The method of claim 21, further comprising the step of:

converting said donut-shaped image detected by said image detection means into at least one user-viewable image of substantially ordinary image proportions, using image processing means.

27. The method of claim 26, wherein said method is used as a method of inspecting pipes.

28. The method of claim 26, wherein said method is used as a method of inspecting bore holes.

29. The method of claim 26, wherein said method is used as a method of conducting surveillance.

30. The method of claim 26, wherein said method is used as a method of performing medical endoscopy.

* * * * *